United States Patent [19]

Gradeff et al.

[11] Patent Number: 4,886,624

[45] Date of Patent: Dec. 12, 1989

[54] COLLOIDAL ALCOHOL-DISPERSIBLE ASSOCIATION COMPLEXES OF CERIC DIOXIDE AND A HYDROXYPHENYL CARBOXYLIC ACID

[75] Inventors: Peter S. Gradeff, Pottersville; Carlos Ramirez, Piscataway, both of N.J.

[73] Assignee: Rhone-Poulenc, Inc., New Brunswick, N.J.

[21] Appl. No.: 87,076

[22] Filed: Aug. 18, 1987

[51] Int. Cl.$^4$ .................... B01J 13/00; C09K 11/07; C09D 3/26; C01F 17/00

[52] U.S. Cl. .................... 252/308; 252/314; 423/21.1; 534/15; 534/16; 106/267

[58] Field of Search ............ 252/308, 309, 312, 314; 534/15, 16

[56] References Cited

U.S. PATENT DOCUMENTS

| | | | |
|---|---|---|---|
| 4,545,923 | 10/1985 | Gradeff et al. | 252/309 |
| 4,599,201 | 7/1986 | Gradeff et al. | 534/15 |
| 4,647,401 | 3/1987 | Gradeff et al. | 252/309 |
| 4,663,439 | 5/1987 | Gradeff et al. | 534/15 |
| 4,699,732 | 10/1987 | Woodhead | 252/314 |

*Primary Examiner*—John F. Terapane
*Assistant Examiner*—John M. Covert

[57] ABSTRACT

A process is provided for preparing colloidal dispersions of alcohol-dispersible association complexes of ceric dioxide and a hydroxyphenyl carboxylic acid having from about seven to about twenty carbon atoms in a molar ratio $CeO_2$/acid of at least about 6:1 which comprises:

(1) mixing
  (a) ceric dioxide comprising ammonium nitrate or ammonium and nitrate ions in an amount within the range from about 3 to about 14% by weight of the ceric dioxide and a member selected from the group consisting of water, methanol, acetic acid and mixtures thereof in an amount usually from about 10 to about 60 g per mole of $CeO_2$, sufficient to effect reaction with
  (b) a hydroxyphenyl carboxylic acid having from about seven to about twenty carbon atoms
  (c) an aliphatic alcohol, such as methanol, isopropanol, 2-ethoxy ethanol, etc.

at a temperature within the range from room temperature to about 100° C., thereby effecting dispersion of the ceric dioxide in the aliphatic alcohol.

10 Claims, No Drawings

COLLOIDAL ALCOHOL-DISPERSIBLE ASSOCIATION COMPLEXES OF CERIC DIOXIDE AND A HYDROXYPHENYL CARBOXYLIC ACID

Metal soaps are well known for their application as driers used in paint and varnish formulations, to accelerate the drying of unsaturated oils such as linseed oil or unsaturated synthetic resins such as alkyd resins. The metallic soap cation is assumed to actively catalyze the oxidation and polymerization processes, while the acid anion serves as a carrier for the metal, conferring oil-solubility, water-insolubility, and compatibility with the other components of the paint.

British Pat. No. 1,236,085 to Steel and Smith, published June 16, 1971, accordingly observes that it is obviously economically advantageous to incorporate as much metal per unit of acid as possible, providing the resulting soap is oil-soluble. This is achieved by the use of "basic" soaps, in which the ratio of metal to acid is greater than the stoichiometric ratio, for example:

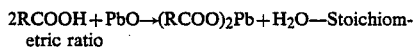

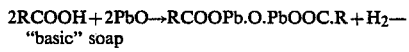

However, the patent comments that in the preparation of "basic" soaps of this type the resulting solution of soap and oil is so highly viscous as to be very difficult to handle, particularly in the blending operations necessary in the manufacture of paint compositions. According to the British patent, this high viscosity can be reduced by reacting the reaction mixture of the carboxylic acid or alkali metal salt thereof with a polyvalent metal salt or metal oxide providing the metal cation of the paint drier.

The polyvalent metal salt or metal oxide used in the process is a salt or oxide of aluminum, barium, copper, iron or magnesium, preferably of zirconium, zinc or manganese, and most preferably of calcium, lead or cobalt. Mixtures of different metal soaps are recommended, inasmuch as certain soaps such as the zinc and calcium soaps do not act as driers on their own, but exert a synergistic effect on other soaps, such as the cobalt or lead soaps. There is no reference to rare earth metal or cerium soaps.

British patent No. 972,804 to Turner, Downs and Harson, published Oct. 14, 1964, describes metal organic soaps which contain aluminum or boron and at least one divalent metal element or metal radical, the aluminum or boron and the divalent metal atoms being linked through oxygen atoms, and at least one carboxylic acid radical. Such metal organic compounds are obtained by condensing alkoxides or aryl oxides of aluminum or boron with acyl oxides of divalent metals or metal radicals. The divalent metals and metal radicals include magnesium, calcium, strontium, barium, zinc, cadmium, iron, cobalt, nickel, lead, copper, manganese and the zirconyl radical, but there is no reference to rare earth metals or radicals, such as cerium. The products have a high metal content, with organic acid radicals present in the proportion of 0.5 to 1.5 equivalents per metal atom. As a result, the products have a higher acid acceptance potential than conventional metallic soaps. These therefore are an example of the kind of "basic" soaps referred to in British patent No. 1,236,085, discussed above.

British patent No. 1,430,347 to Collins and Pearl, published Mar. 31, 1976, notes that the normal of "basic" metal soaps of synthetic carboxylic acids have been compounds analogous to those previously derived from natural acids, or, in using different synthetic carboxylic acids as they become available, have presented compounds with a more or less homologous if not isomeric relation to each other. Collins et al propose a departure from this prior art, using a different method of preparation, and a different composition, which results in a different character and properties of the resulting drier product or metal soap.

The prior art procedure according to Collins et al involves fusion or precipitation methods. The reactant acid can be dissolved in an appropriate inert solvent, usually a hydrocarbon solvent such as mineral spirits, to which then is added the desired metal compound, usually in the form of an appropriate oxide or inorganic compound or salt, with heating at an appropriate temperature to promote the reaction. This results in a hydrocarbon solution of the soap, and the solvent can be distilled off to increase the metal concentration to the desired value.

The Collins et al process utilizes a carboxylic acid or acid mixture which may be natural in origin, or derived from a natural product, or a synthetic product, and mixes this with a glycol ether or glycol or like polyol, with addition also of a metal compound such as the metal powder or an oxide, hydroxide, acetate, or carbonate of the metal. This mixture is then heated at a temperature from 65° to 143° C. until the metal compound disappears, after which water is distilled off, the reaction mixture filtered, and excess glycol and glycol ether distilled off to an appropriate desired concentration or condition.

The equivalents ratio of metal to glycol ether or polyol is at least 0.5, but a significant amount of the glycol ether or polyol must be retained in the product when it is desired to maintain fluidity. The equivalents ratio for the metal moiety and the acid moiety is at least 1.0, and when the metal is lead, at least 1.5, and ratios of 2 and higher are easily obtained for lead. Barium, nickel and manganese soaps as well as cobalt soaps have been prepared by this method, in addition to lead. There is however no reference to rare earth metals, such as cerium.

The patentees note that their product and process are clearly distinct from the use of varying amounts of glycol or glycol ether merely to reduce the viscosity of the lead carboxylate, as in British patent No. 1,148,998, or to stabilize soap solutions, as in fisher U.S. patent No. 2,007,553. These products are marketed by the assignee, Mooney Chemicals, Inc.

Gamlen Europe SA, French patent No. 76 22426, publication No. 2,359,192, published Feb. 17, 1978, and British patent No. 1,571,210 published July 9, 1980, provodes organic cerium salts soluble in organic solvents characterized by a ratio R of the number of acid equivalents to the number of cerium atoms of between 0.2 and 1, the number of acid equivalents meaning the number of acid molecules when the acid used is monofunctional, and this number has to be doubled or trebled in the case of diacids or triacids, and more generally multiplied by the number of acid functions in the case of a polyacid. The cerium compounds thus provided require a much smaller amount of acid than the amount used previously with the same effectiveness, and also solutions of high metal concentration reaching 500 g/l can be obtained which remain fluid and are capable of being handled without difficulty, while at the same time remaining completely soluble in hydrocarbon media.

The organic acid can be any of $RCOOH$, $RSO_3H$, $ROSO_3H$, $ROPO_3H_2$ or $(RO)_2PO_2H$, where R is a hydrocarbon radical having at least seven carbon atoms. The organic acid radical can be a linear or branched aliphatic radical or a cycloaliphatic radical, which is optionally alkylated, or an aromatic radical, which is optionally alkylated. The cerium organic acid salts may contain at least one other rare earth metal element, in addition, in an amount up to 25% of the total rare earth element content including cerium. These compositions can be provided in the form of organic solvent solutions of the cerium organic acid salt or mixture thereof containing more than 200 g/l of the composition. This composition can be included in paints or varnishes or liquid fuels.

The method for preparing these cerium organic acid salts or mixtures thereof comprises reacting (in organic or an aqueous organic medium) the organic acid and freshly prepared cerium hydroxide $Ce(OH)_3$ under such conditions that the resultant cerium organic acid salts have a ratio r of between 0.2 and 1. The reaction is preferably effected with heating, and preferably the organic medium is a hydrocarbon. After several hours, part of the water formed by the reaction separates spontaneously. After the reaction, to assist in the separation of water from the reaction medium, a further solvent can be added, such as a glycol, an alcohol or an alkyl glycol. The solution thus obtained can have its concentration adjusted by addition of a suitable hydrocarbon.

In the working Examples, cerium hydroxide $Ce(OH)_3$ is obtained by precipitating cerium nitrate with aqueous ammonia. The precipitate is washed with water until nitrate ion has disappeared, and then filtered until it contains only 15% water. The cerium hydroxide is reacted with 130 g of usual-grade oleic acid in white spirits at 80° C. After stirring for four hours, glycol is added, the separated water is eliminated, and then butyl-glycol is added, after which white spirit is added to form the final solution.

It will be noted that it is with the cerous salts, not the ceric salts, that the patentees are concerned.

French patent application No. 81 09214, U.S. Pat. No. 2,482,075, and related cases therein discussed refer to the preparation of aqueous dispersions of cerium compounds that can be easily dispersed. By heating hydrated ceria containing $NO_3^-$, $Cl^-$ or $ClO_4^-$ for 1 to 2 hours at temperatures of from 200° to 450° C., a material is obtained that is dispersible in aqueous solutions. No indications are given, however, that the material can be dispersed in organic media.

Kirk-Othmer, *Encyclopedia of Chemical Technology*, (Second Edition), Volume 4, p. 850, indicate that hydrated ceric oxide, also referred to as hydrous ceric oxide or cerium hydroxide $CeO_2xH_2O$, where x is a number from ½ to 2, forms as a gelatinous precipitate when sodium or ammonium hydroxides are added to solutions of ceric salts. It is usually referred to as hydrous ceric oxide. When the precipitate is dried, a yellow hydrated oxide containing 85 to 90% $CeO_2$ results. Granular ceric hydroxide may be made by boiling insoluble cerium salts with concentrated sodium hydroxide, followed by washing and drying. The composition and structure of these compounds depend on the method of preparation, and in many cases are uncertain. For this reason, it is common practice to express the composition in terms of equivalent $CeO_2$.

Cerous hydroxide $Ce(OH)_3$ forms as a white or off-white gelatinous precipitate when solutions containing cerous ion $Ce^{3+}$ are made alkaline. When allowed to stand for any length of time, a violet surface layer of cerosoceric hydroxide appears.

Ceric oxide $CeO_2$ usually is made by igniting cerous oxalate or cerous or ceric hydroxide in air. Ceric oxide is insoluble in acids, but dissolution is hastened by adding a small quantity of a reducing agent, such as an iodide or hydrogen peroxide. Eventually, strong nitric or sulfuric acid reacts upon heating.

In many applications, hydrated ceric oxide may be substituted for ceric oxide. However, unlike cerous hydroxide, which is a classic type of metal hydroxide similar to $Pb(OH)_2$, $Fe(OH)_3$, etc., ceric hydroxide is actually hydrated ceric dioxide, also called hydrous ceric oxide, as noted above. Accordingly, the term "ceric dioxide" as used in this specification and claims will be understood also to be inclusive of ceric hydroxide, hydrated ceric dioxide and, hydrous ceric oxide, which are all different names for essentially the same chemical, ceric dioxide.

If pure ceric oxide is stirred and heated at a temperature in the range of from 60° to 200° C. in the presence of an aliphatic solvent, such as petroleum spirits, or an aromatic solvent, such as toluene, and in the presence of a carboxylic acid such as oleic, palmitic acid, or dodecylbenzene sulfonic acid, there is no dispersion. Neither is there any other reaction with any other carboxylic acid, or alkyl or alkylaryl sulphonic acid.

Gradeff, Charte, Schreiber and Davison U.S. Pat. No. 4,545,923, patented Oct. 8, 1985, provides an entirely new type of high cerium content colloidal ceric dioxide, which can be dispersed in organic liquids, particularly organic solvents, as well as high cerium content compositions containing such colloidal ceric dioxide dispersed in an organic liquid. The high cerium content dispersions in accordance with the invention are true dispersions as demonstrated by transmission electron microscopy. The term "dispersed cerium dioxide" as used in this specification and claims indicates that the ceria particles are of colloidal dimensions, and therefore exist in the form of a colloidal dispersion in organic liquids, but this does not exclude the presence of ceria. in solution, in addition to or instead of the colloidally dispersed ceria. Transmission electron microscopy of the hydrated ceria before treatment in accordance with the invention does not show particles of colloidal dimensions. The conversion of this ceria to colloidal size particles is obtained during the treatment.

FIG. 1 of the patent is a transmission electron microphotograph showing the crystalline particle form of a typical ceric dioxide prior to treatment in accordance with the process of the patent; and FIG. 2 of the patent is a transmission electron microphotograph showing the particle form of the ceric dioxide of FIG. 1 after treatment in accordance with the process of the patent.

This form of colloidal ceric dioxide is obtained from ceric dioxide prepared especially for use as a starting material in the process of the patent in such a way as to contain in physical association therewith:

(1) from about 3 to about 14% of ammonium nitrate; and (2) at least one of water, methanol, acetic acid and mixtures of any two or three thereof in an amount within the range from about 10 to about 60 g per mole of $CeO_2$.

Both (1) and (2) are essential, and must be present. This material is referred to as "active ceric dioxide" or "active $CeO_2$".

It has been established by experimental evidence that the patented process can be regarded as effecting a physical adsorption-addition reaction (as contrasted to a chemical substitution-elimination reaction, such as a salt formation) of the organic acid, possibly interstitially, or as an inclusion by chemisorption, into the ceric dioxide, whether crystalline or noncrystalline. This association is formed upon the breakdown of the large agglomerates of ceric dioxide into crystallites with diameters of about 50 Å while heating the active ceric dioxide as above defined, and in the presence of a solubilizing organic acid of ten to forty carbon atoms and an appropriate organic liquid at a temperature within the range from about 60° to about 200° C., for a sufficient time, usually from 1 hour to about 24 hours, to effect the reduction of the agglomerates to colloidal size crystallites and their association with the solubilizing acid, followed by removal of the water, methanol or acetic acid released, and filtering off the salts that separate upon cooling.

The $CeO_2$-acid association complex can be isolated from such colloidal solutions in solid colloidal particle form. Transmission electron microscopy of the colloidal solutions shows perfectly dispersed crystallites of 50 Å. Provided it is kept in a closed container, the complex remains stable for some time. When mixed with an appropriate organic liquid, a colloidal dispersion is obtained at once.

This association complex is however not dispersible in alcohol to form a colloidal dispersion, and cannot be used where alcohol dispersibility is a prerequisite. An alcohol-dispersible material would fill a specific commercial need.

The process of Pat. No. 4,545,923 comprises:
(1) heating
(a) ceric dioxide comprising ammonium nitrate in an amount within the range from about 3 to about 14% by weight of the ceric dioxide and a member selected from the group consisting of water; methanol; acetic acid; and mixtures thereof in an amount of at least 10 g per mole of $CeO_2$ sufficient to effect reaction with
(b) an organic acid having from about ten to about forty carbon atoms; and
(c) an organic liquid selected from the group consisting of aliphatic and aromatic hydrocarbons; aliphatic and cycloaliphatic ethers; and aliphatic and cycloaliphatic ketones at a temperature within the range from about 60° to about 200° C., thereby forming a colloidal dispersion in the organic liquid of the ceric dioxide and associated organic acid; and
(2) removing any water, methanol and acetic acid released during the heating and separating any undissolved solid particles.

In accordance with the present invention, it has been determined that if the organic acid is a hydroxy phenyl carboxylic acid and the organic solvent an aliphatic alcohol, or mixed alcohol-ether or alcohol-ketone, the association complex that is obtained is alcohol dispersible and not dispersible in hydrocarbon solvents.

The invention according provides a process for preparing colloidal dispersions of alcohol-dispersible association complexes of ceric dioxide and a hydroxy phenyl carboxylic acid having from about seven to about twenty carbon atoms in a molar ratio $CeO_2$/acid of at least about 6:1 which comprises:
(1) mixing
(a) ceric dioxide comprising ammonium nitrate in an amount within the range from about 3 to about 14% by weight of the ceric dioxide and a member selected from the group consisting of water; methanol; acetic acid; and mixtures thereof in an amount of at least 10 g per mole of $CeO_2$ sufficient to effect reaction with
(b) a hydroxy phenyl carboxylic acid having from about seven to about twenty carbon atoms; and
(c) an aliphatic alcohol, including aliphatic alcohol-ethers and aliphatic alcohol ketones at a temperature within the range from room temperature about 20° C. to about 100° C., thereby forming a colloidal dispersion in the alcohol of the ceric dioxide and associated organic acid; and
(2) removing any water, methanol and acetic acid released during the heating and separating any undissolved solid particles.

Both (1) and (2) are essential, and must be present. This material is referred to as "active ceric dioxide" or "active $CeO_2$".

Exactly as in the case of the patented process, the process of the invention can be regarded as effecting a physical adsorption-addition reaction (as contrasted to a chemical substitution-elimination reaction, such as a salt formation) of the hydroxyphenyl carboxylic acid, possibly interstitially, or as an inclusion by chemisorption, into the ceric dioxide, whether crystalline or noncrystalline. This association complex is alcohol-dispersible, in the present case, due to the presence of the solubilizing hydroxyphenyl carboxylic acid of seven to twenty carbon atoms, and an aliphatic alcohol at a temperature within the range from about 20° to about 100° C., for a sufficient time, usually less than one hour to about 24 hours, to effect the reduction of the agglomerates to colloidal size crystallites and their association with the solubilizing acid and dispersion in the alcohol, followed by removal of the water, methanol or acetic acid released, and filtering off the salts that separate upon cooling.

These alcohol dispersions are composed of dispersed colloidal particles. The alcohol-dispersible $CeO_2$-acid association complex can be isolated from such colloidal dispersions in solid colloidal-size particle form. Transmission electron microscopy of the colloidal dispersions shows the dispersions to be very uniform and homogeneous. Provided it is kept in a closed container, the complex remains stable for some time. When mixed with an appropriate alcohol, a colloidal dispersion is obtained at once.

The starting ceric dioxide can be pure ceric dioxide, hydrous ceric dioxide, or hydrated ceric dioxide, but it is essential that the ceria starting material contain from about 3 to about 14% by weight ammonium nitrate. The ammonium nitrate cannot be merely in admixture with or added to the ceria, but must be in close physical association with the ceria, possibly as an inclusion of ammonium nitrate as the salt molecule and/or as ammonium and nitrate ions in the structure of the agglomerates found in the course of preparation of hydrated ceria. The second requirement is the presence in the system of the indicated amount of water, or methanol, or acetic acid, or mixture thereof.

The starting ceric dioxide suitable for making the products of the invention is commercially available from Rhone-Poulenc. It can also be prepared by processes described in the patents, for instance, cerous nirate or cerous carbonate treated with aqueous nitric acid followed by $NH_4OH$—$H_2O_2$ treatment, as indicateed in French patent publication No. 2,482,075. For the purpose of this invention, the ceric dioxide that is recovered, for example, by filtration, centrifuging, or other separation technique, does not need to be washed, but if washed, it is not washed sufficiently to remove the occluded ammonium nitrate. It thus has in physical association from about 3 to about 24% residual ammonium nitrate, and also some cerium nitrate. The amount of nitrate may vary, depending on the process parameters selected in the manufacture, the amount of residual mother liquor, or the extent of partial washing, if applied. Understandably, when the base used for the precipitation is $NH_4OH$, the ions carried by the ceria will be those of $NH_4^+$ and $NO_3^-$.

The set material as it comes from the filter contains also a variable amount of water. If the second requirement is to be met by water present, it may be noted that at least about 10 g of water/mole of $CeO_2$ is necessary for the wet material to be useful in the invention. Normally, the amount of water retained in the freshly prepared hydrated ceria is from about 10 to 20%. Obviously, a higher water content can be present, but is a nuisance, since it has to be removed later on in the process.

Surprisingly, while methanol can be used in substitution for water, other lower alcohols such as ethanol are not effective, and cannot be substituted for the methanol.

Similarly acetic acid is the only acid that can be substituted for the water or the methanol; the organic acid used for preparation of the association complex cannot be used. The acetic acid as the water or the methanol has evidently a special function in the still not fully understood mechanism of breaking the agglomerates to colloidal size $CeO_2$, followed by the addition of the solubilizing acid.

The amount of water or methanol or acetic acid or mixture thereof is from at least 10 up to about 60 g/mole $CeO_2$.

Prolonged drying of the ceria should not be carried out at such high temperatures, as for instance at 375° C. or above, that ammonium nitrate decomposes, since then the $NH_4NO_3$ content in the resulting ceria could drop below the required minimum amount, and the resulting ceria material may no longer be useful in the process of the invention, even with the addition of water, methanol, or acid, and even free ammonium nitrate.

The aliphatic alcohol reaction medium used in the process can be an inert aliphatic alcohol or mixture thereof that is liquid at the selected reaction temperature, such as for example, methanol, ethanol, propanol, isopropanol, butanol, isobutanol, secbutanol, tert-butanol, pentanol, isopentanol, hexanol, heptanol, octanol, 2-ethyl hexanol, nonanol and decanol.

Aliphatic and aromatic hydrocarbon, ether and ketone solvents cannot be used, since the reaction with the hydroxyphenyl carboxylic acid does not proceed in such a medium. However, the reaction does proceed with alcohols containing ether groups in addition to the alcoholic hydroxyo, such as 2-ethoxy ethanol, 3-propoxy propanol, methyl ether of diethylene glycol, ethyl ether of diethylene glycol, etc.

The alcohol or solvent system will be selected taking into consideration the solubilizing hydroxphenyl carboxylic acid that is used, and the reaction temperature, as well as the ultimate application of the colloidal dispersion. In some cases, a mixture of alcohol solvents is preferable. The amount of alcohol solvent evidently determines the final concentration. Dispersions containing up to about 50% $CeO_2$ are prefectly fluid. It is therefore more economical and convenient to prepare more highly concentrated dispersions which later on can be diluted for use. For this reason the amount of alcohol is not critical.

The hydroxyphenyl carboxylic acid forming the alcohol-soluble physical association complex has the formula:

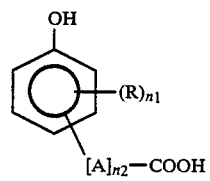

wherein:

R is hydrogen or lower having from one to about four carbon atoms;

A is a bivalent linking saturated or unsaturated hydrocarboon group having from one to about ten carbon atoms;

$n_1$ is 0, 1 or 2; and $n_2$ is 0 or 1.

The A—COOH can be meta or para to the OH. Preferably, the A—COOH group is para to the OH.

Exemplary R alkyl groups include methyl, ethyl, propyl, isopropyl, butyl, isobutyl, sec-butyl and tert-butyl.

Exemplary A linking groups include

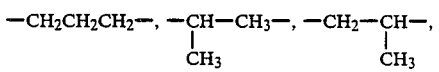

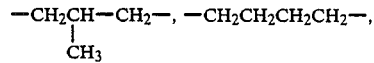

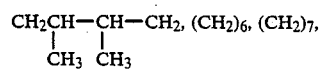

Exemplary are p-hydroxy phenyl acetic acid, m-hydroxy phenyl acetic acid, p-hydroxyphenyl propionic acid, m-hydroxy phenyl propionic acid, p-hydroxy phenyl butyric acid, p-hydroxybenzoic acid, and p-hydroxy cinnamic acid.

The type of solubilizing organic acid used often determines the maximum amount of $CeO_2$ that can be dissolved.

The organic acid is used in an amount of at least 0.15 mole per mole of $CeO_2$, inasmuch as the $CeO_2$-acid physical association complex contains a ratio of $CeO_2$:acid of 6:1, as evidenced by the composition of the isolated solid form. While smaller amounts of acid can be used, an incomplete dispersion of the ceria may result, or a relatively unstable dispersion that will tend to deposit CeO$_2$. More than 0.25 mole or organic acid can be used, but may not be necessary.

The presence of water, or methanol, or acetic acid, or mixture thereof is essential during the digestion time period, but their role is not well understood. At least it can be said that they assist in the expulsion of the nitrate ions in a manner resulting in the reduction of the CeO$_2$ agglomerations to colloidal size particles. The highly active surface of the crystallites then absorbs the acid that renders them alcohol-dispersible. If any of the essential activating volatile components, such as water, methanol, or acetic acid is removed from the system before the desired processes have taken place, the reaction may not take place at all, or can be incomplete.

Commercial grade hydrated ceria contain other rare earths as impurities. In some cases the presence of such impurities may be desirable for the beneficial synergistic effects they may exhibit. Mixtures of ceria containing up to about 10% of other rare earths can also be used in this process.

The overall reaction can take from less than one hour up to about 24 hours or longer, while heating (if desired) and agitating at a temperature within the range from about 20° to about 100° C.

A preliminary heating of the starting ceria dioxide either as an aqueous slurry or in a mixture with the aliphatic alcohol at a temperature within the range from about 60° to about 200° C. for several hours followed by addition of the hydroxy phenyl carboxylic acid used in the formation of the physical association complex may result in a significantly faster solubilization rate. Electron microscopic examination of the heated material has revealed that no size reduction of the ceria particles has taken place, and thus it is believed that during the heating the crystalline bridges of ammonium nitrate and/or NH$_4$+ and NO$_3$− ions are weakened, but not broken. It appears that uner the mild reaction conditions of the treatment, reduction of the ceria to colloidal size is effected by adsorption of the hydroxyphenyl carboxylic acid onto the ceria particles, which also renders the colloidal particles alcohol-dispersible. By "alcohol-dispersible" is meant dispersible in lower aliphatic alcohols such as methanol, ethanol, propanols, butanols, pentanols and hexanols. The colloidal dispersions produced by the described process thus are believed to contain the solubilizing acid as the free acid, and not in any ionized form. Thus, the cerium dioxide products described herein are not to be considered as cerium soaps, since these soaps are essentially cerium salts of ionized fatty acids.

The following Examples in the opinion of the inventors represent preferred embodiments of the invention.

EXAMPLES 1 to 7

A. Preparation of the Colloidal Dispersion

A solution of p-hydroxyphenyl acetic acid (9.42 g, 0.061 mole) in 35.00 g of 2-ethoxyethanol was charged in a 250 ml three-necked reaction flask equipped with condenser, stirrer and thermometer. To this solution was added with stirring (CeO$_2$xH$_2$O) 55.09 g at 63.03% cerium, equivalent to 0.248 mole. A light brown slurry was formed, which transformed itself to a dark brown solution in a period ranging of about 40 minutes at room temperature. The mixture was slowly heated to 90° C., to ensure complete dispersion, and then allowed to cool to room temperature; 12.50 g of 2-ethoxyethanol was added, a Dean stark trap was attached and H$_2$O removed azeotropically (98° C.) under oil pump vacuum. Total 7.62 g of H$_2$O was removed. The solution was cooled to room temperature and filtered. Ash analysis of th filtrate indicated 34.04% cerium.

B. Isolation of the Alcohol-dispersible CeO$_2$ Acid Complex in a Solid Form 20 grams of the above alcohol-dispersible product was dropped under stirring into 40 g of acetone. The brownish precipitate was filtered and washed 3 times with 30 ml of acetone, and dried under vacuum for 24 hours. Ash analysis indicated 65.86% cerium, which indicates a composition comprising 4 moles CeO$_2$ and one mole of the acid (Theory 66.5%).

Following the same procedure, using the same active CeO$_2$, an amount of acid of between 0.022 and 0.25 mole per mole of CeO$_2$, and a solvent in an amount so as to have the desired final concentration, several experiments were carried out using different acids and solvents shown in Table I. In all cases, complete dispersion of the ceria was achieved, and the reaction product was found to be totally dispersible in common alcohols.

TABLE I

| Example No. | Acid | Solvent | Dispersibility MeOH/ EtOH/ Isopropanol | AMSCO/ Heptane/ Toluene |
|---|---|---|---|---|
| 1 | p-hydroxy phenyl acetic acid | Ethoxy-ethanol | YES | NO |
| 2 | p-Hydroxy cinnamic acid | 2-Ethoxy-ethanol | YES | NO |
| 3 | m-Hydroxy cinnamic acid | 2-Ethoxy-ethanol | YES | NO |
| 4 | p-Hydroxy-benzoic acid | 2-Ethoxy-ethanol | YES | NO |
| 5 | m-Hydroxy-benzoic acid | 2-Ethoxy-ethanol | YES | NO |
| 6 | p-Hydroxy phenyl acetic acid | Methanol | YES | NO |
| 7 | p-Hydroxy phenyl acetic acid | 2-Octano methanol | YES | NO |

Having regard to the foregoing disclosure, the following is claimed as the inventive and patentable embodiments thereof:

1. An association complex comprising ceric dioxide and a hydroxyphenyl carboylic acid having from about seven to about twenty carbon atoms in a molar ratio CeO$_2$/acid of at least about 6:1.

2. An association complex according to claim 1 in which the hyroxyphenyl carboxylic acid is p-hydroxy benzoic acid.

3. An association complex accoding to claim 1 in which the hyroxyphenyl carboxylic acid is p-hydroxy phenyl acetic acid.

4. An association complex according to claim 1 in which the hydroxyphenyl carboxylic acid is p-hydroxy cinnamic acid.

5. An association complex according to claim 1 in which the hydroxyphenyl carboxylic acid has the formula:

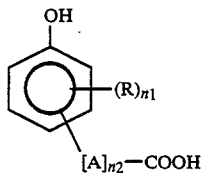

wherein:

R is hydrogen or lower alkyl having from one to about four carbon atoms;

A is a bivalent linking saturated or unsaturated hydrocarbon group having from one to about ten carbon atoms;

$n_1$ is 0, 1 or 2;

$n_2$ is 0 or 1; and the A—COOH is in the para or meta position with respect to the OH.

6. A colloidal dispersion in an aliphatic alcohol comprising an association complex according to claim 1.

7. A colloidal dispersion in an aliphatic alcohol comprising an association complex according to claim 2.

8. A colloidal dispersion in an aliphatic alcohol comprising an association complex according to claim 3.

9. A colloidal dispersion in an aliphatic alcohol comprising an association complex according to claim 4.

10. A colloidal dispersion in an aliphatic alcohol comprising an association complex according to claim 5.

* * * * *